US012118779B1

(12) United States Patent
Hu et al.

(10) Patent No.: US 12,118,779 B1
(45) Date of Patent: Oct. 15, 2024

(54) SYSTEM AND METHOD FOR ASSESSING STRUCTURAL DAMAGE IN OCCLUDED AERIAL IMAGES

(71) Applicant: UIPCO, LLC, San Antonio, TX (US)

(72) Inventors: Yangqiu Hu, San Antonio, TX (US); David Lamar Rogers, San Antonio, TX (US); Ting Lu, San Antonio, TX (US); Jess W. Gingrich, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 208 days.

(21) Appl. No.: 17/936,551

(22) Filed: Sep. 29, 2022

Related U.S. Application Data

(60) Provisional application No. 63/250,526, filed on Sep. 30, 2021.

(51) Int. Cl.
| | |
|---|---|
| *G06V 20/10* | (2022.01) |
| *G06Q 10/10* | (2023.01) |
| *G06V 10/44* | (2022.01) |
| *G06V 10/764* | (2022.01) |
| *G06V 10/774* | (2022.01) |
| *G06V 20/17* | (2022.01) |
| *G16H 30/40* | (2018.01) |

(52) U.S. Cl.
CPC ........... *G06V 20/176* (2022.01); *G06Q 10/10* (2013.01); *G06V 10/44* (2022.01); *G06V 10/764* (2022.01); *G06V 10/774* (2022.01); *G06V 20/17* (2022.01); *G16H 30/40* (2018.01)

(58) Field of Classification Search
CPC ...... G06V 20/176; G06V 20/17; G06V 10/44; G06V 10/774; G06V 10/764; G16H 30/40; G06Q 10/10
See application file for complete search history.

(56) References Cited

U.S. PATENT DOCUMENTS

| | | | |
|---|---|---|---|
| 10,311,302 B2 * | 6/2019 | Kottenstette | ......... G06V 20/176 |
| 10,366,288 B1 * | 7/2019 | Kottenstette | ........ G06F 18/2413 |
| 10,521,902 B2 * | 12/2019 | Avendi | ...................... G06T 3/02 |
| 10,593,033 B2 * | 3/2020 | Niculescu-Mizil | ... G06F 18/211 |

(Continued)

OTHER PUBLICATIONS

Arunnehru, Springer, 2015, pp. 307-316.*

(Continued)

*Primary Examiner* — Michael I Ezewoko
(74) *Attorney, Agent, or Firm* — Plumsea Law Group, LLC

(57) ABSTRACT

A system and method for processing occluded aerial images of structures to assess structural damage is disclosed. The system employs a generative model that is trained on data created by adding occlusive features to clear aerial images. Both the clear images and their simulated occluded counterparts (image pairs) are inputted into the generative model as training data, and the model learns to recognize and discriminate patterns between the pairs. This process is fully automated and does not require manual labeling. Following training, the model is capable of receiving real (non-simulated) occluded images and generating a clarified image that can reveal structural details previously not apparent to automatically determine a damage classification for the property.

20 Claims, 8 Drawing Sheets

(56) References Cited

U.S. PATENT DOCUMENTS

| | | | | |
|---|---|---|---|---|
| 10,600,184 | B2* | 3/2020 | Golden | G06T 7/149 |
| 10,643,072 | B2* | 5/2020 | Kottenstette | G06V 10/764 |
| 10,733,722 | B2* | 8/2020 | Niculescu-Mizil | G06F 18/24 |
| 10,835,761 | B2* | 11/2020 | Bériault | A61N 5/1048 |
| 10,839,506 | B1* | 11/2020 | Raghu | G06T 7/0004 |
| 10,842,445 | B2* | 11/2020 | Wang | G06T 7/35 |
| 10,853,937 | B2* | 12/2020 | Niculescu-Mizil | G06V 10/454 |
| 10,871,536 | B2* | 12/2020 | Golden | G06N 3/084 |
| 10,891,511 | B1* | 1/2021 | Jiang | G06V 10/758 |
| 10,902,598 | B2* | 1/2021 | Golden | G06N 3/08 |
| 10,967,202 | B2* | 4/2021 | Van Heteren | A61N 5/1081 |
| 11,042,968 | B2* | 6/2021 | Xu | G06F 18/214 |
| 11,083,913 | B2* | 8/2021 | Lachaine | G16H 50/70 |
| 11,151,378 | B2* | 10/2021 | Kottenstette | G06F 18/2413 |
| 11,182,896 | B2* | 11/2021 | Avendi | G06V 10/764 |
| 11,328,402 | B2* | 5/2022 | Tang | G06T 7/0002 |
| 11,394,927 | B2* | 7/2022 | Buibas | G06Q 10/087 |
| 11,430,167 | B2* | 8/2022 | Zhang | G06T 5/50 |
| 11,436,484 | B2* | 9/2022 | Farabet | G06V 10/454 |
| 11,491,348 | B2* | 11/2022 | Bériault | G06T 7/0014 |
| 11,547,874 | B2* | 1/2023 | Lachaine | A61N 5/1039 |
| 11,551,353 | B2* | 1/2023 | Golden | G06N 3/08 |
| 11,551,394 | B2* | 1/2023 | Biswas | G10L 15/02 |
| 11,557,036 | B2* | 1/2023 | Liao | G06T 7/30 |
| 11,568,639 | B2* | 1/2023 | Kottenstette | G06V 10/764 |
| 11,651,487 | B2* | 5/2023 | Arafati | G06N 3/045 382/128 |
| 11,676,007 | B2* | 6/2023 | Lovell | G06F 30/20 706/25 |
| 11,676,247 | B2* | 6/2023 | Zimmer | G06T 3/4069 382/299 |
| 11,741,605 | B2* | 8/2023 | Liao | G06T 7/30 |
| 11,783,627 | B2* | 10/2023 | Dagdeviren | G06V 40/174 382/103 |
| 11,789,453 | B2* | 10/2023 | Chowdhary | G06T 7/155 382/110 |
| 11,843,624 | B1* | 12/2023 | Estep | G06N 3/09 |
| 11,922,320 | B2* | 3/2024 | Jaipuria | G06N 3/094 |
| 11,940,519 | B2* | 3/2024 | O'Brien | G01R 33/56 |
| 11,947,682 | B2* | 4/2024 | Zhang | G06F 9/547 |
| 11,954,886 | B2* | 4/2024 | Taamazyan | G06V 10/147 |
| 11,966,673 | B2* | 4/2024 | Kristensen | G06N 3/045 |
| 2018/0260793 | A1* | 9/2018 | Li | G06Q 40/08 |
| 2018/0293552 | A1* | 10/2018 | Zhang | G06V 10/25 |
| 2018/0374204 | A1* | 12/2018 | Manhart | G06T 3/14 |
| 2018/0374207 | A1* | 12/2018 | Niculescu-Mizil | G06F 18/211 |
| 2018/0374569 | A1* | 12/2018 | Niculescu-Mizil | G06F 18/214 |
| 2019/0244337 | A1* | 8/2019 | Niculescu-Mizil | G06F 18/214 |
| 2019/0303759 | A1* | 10/2019 | Farabet | G05D 1/00 |
| 2020/0111204 | A1* | 4/2020 | Cosatto | G06T 7/0004 |
| 2020/0410687 | A1* | 12/2020 | Siemionow | G06T 7/62 |
| 2021/0158041 | A1* | 5/2021 | Chowdhary | G05D 1/0272 |
| 2021/0233273 | A1* | 7/2021 | Spurr | G06F 18/217 |
| 2021/0286923 | A1* | 9/2021 | Kristensen | G01S 7/412 |
| 2021/0294944 | A1* | 9/2021 | Nassar | G06F 30/27 |
| 2021/0339046 | A1* | 11/2021 | Lachaine | A61N 5/1037 |
| 2021/0357555 | A1* | 11/2021 | Liu | G06F 30/27 |
| 2022/0066544 | A1* | 3/2022 | Kwon | G06V 40/23 |
| 2022/0084270 | A1* | 3/2022 | Zhang | G06V 40/103 |
| 2022/0198617 | A1* | 6/2022 | Gafni | G06V 40/174 |
| 2022/0198784 | A1* | 6/2022 | Toporek | G06V 10/7747 |
| 2023/0004801 | A1* | 1/2023 | Farabet | G06V 10/764 |
| 2023/0106383 | A1* | 4/2023 | Yao | G06T 3/4046 382/299 |
| 2023/0106440 | A1* | 4/2023 | Golden | G06V 10/82 382/131 |
| 2023/0126829 | A1* | 4/2023 | Grigorev | G06N 3/045 345/419 |
| 2023/0154181 | A1* | 5/2023 | Lorenzen | G06V 10/764 382/103 |
| 2023/0289596 | A1* | 9/2023 | Lovell | G06N 3/047 |
| 2023/0368383 | A1* | 11/2023 | Liao | G06T 7/30 |
| 2024/0012912 | A1* | 1/2024 | Zhang | G06F 9/547 |
| 2024/0013067 | A1* | 1/2024 | Azarafrooz | G06F 21/602 |
| 2024/0029415 | A1* | 1/2024 | Shanbhag | G06V 10/82 |
| 2024/0061440 | A1* | 2/2024 | Chowdhary | G06N 20/10 |
| 2024/0078363 | A1* | 3/2024 | Nassar | G06F 11/3684 |
| 2024/0087130 | A1* | 3/2024 | Siemionow | G06F 3/0484 |
| 2024/0092390 | A1* | 3/2024 | Philion | B60W 60/0011 |
| 2024/0161479 | A1* | 5/2024 | Tyan | G06V 10/42 |

OTHER PUBLICATIONS

Chen, Elsevier, 2019 pp. 93-107.*
Cheng, Elsevier, 2014, pp. 54-68.*
Cledat, Elsevier, 2020, pp. 24-38.*
He, Elsevier, 2021, pp. 1-11.*
Image Analysis And Recognition, Campilho, Springer pp. 845-852.*
Martel, Spinger, 2020, pp. 128-137.*
Xu, Elsevier, 2021, pp. 1-12.*
Xu, Elsevier, 2021, pp. 266-277.*

* cited by examiner

SYSTEM AND METHOD FOR ASSESSING STRUCTURAL DAMAGE IN OCCLUDED AERIAL IMAGES

CROSS-REFERENCE TO RELATED APPLICATION

This application claims the benefit of U.S. Provisional Patent Application Ser. No. 63/250,526 filed on Sep. 30, 2021 and titled "System and Method for Assessing Structural Damage in Occluded Aerial Images", the disclosure of which is incorporated by reference in its entirety.

TECHNICAL FIELD

The present disclosure generally relates to structural damage assessments, and in particular to a system and method for assessing damage done to structures using aerial imagery, machine learning techniques, and generative imaging.

BACKGROUND

Following disasters such as floods, hurricanes, fires, and tornadoes, entities that insure properties in the disaster area may need to survey the area in order to assess any damage that has impacted one or more insured properties. For large scale disaster areas, aerial imagery may be used to assess damage. Specifically, an aerial vehicle may fly over the disaster area collecting continuous images that may later be combined into a single orthomosaic image. These images can be used to identify generally whether a structure has been damaged. However, in many cases—particularly where a natural disaster such as a wildfire or hurricane has occurred—imagery of the disaster area can be occluded by smoke, haze, clouds, etc. In such cases, determining whether a structure was damaged becomes a time-consuming and resource intensive task, typically requiring a human agent to visit the structure in person to more closely examine the effects of the disaster. Even when such examinations are necessary, local environmental conditions following a disaster can prevent access to the structure for several days or weeks. This process can lead to delays for homeowners and other insured entities in receiving much needed relief or support. The ability to quickly determine whether a structure has experienced a substantial loss, without the need for on-site manual inspections or other time-intensive tasks, is highly desirable.

There is a need in the art for a system and method that addresses the shortcomings discussed above.

SUMMARY

In one aspect, a method of identifying property damage in occluded aerial imagery is disclosed. The method includes a first step of receiving, at a damage classification system, first data including a first occluded image of a first property comprising at least a first structure, wherein the first structure is veiled in the first occluded image, and a second step of feeding, at the damage classification system, the first occluded image to a generative model to generate a first reconstructed image in which the first structure is unveiled. The method also includes a third step of extracting, at the damage classification system, a first feature from the first reconstructed image, and a fourth step of estimating, by the damage classification system, damage to the first property based on at least the first feature. A fifth step includes classifying, by the damage classification system, the first property depicted in the first reconstructed image under a damage category based on the estimated damage, and a sixth step includes causing to be presented, at a computing device, the damage category. At least a portion of the method is performed by a processing unit.

In another aspect, a method of clarifying occluded images to determine property damage is disclosed. The method includes a first step of receiving, at a damage classification system, a training dataset, the training dataset comprising pairs of images, each pair including a first image and a second image, the first image providing a high visibility picture of a property, the second image providing a low visibility picture of the same property in the same position as in the first image. A second step includes training, at the damage classification system, a generative model using the training dataset to produce high visibility pictures from occluded imagery. The method also includes a third step of receiving, at the damage classification system, first data including a first occluded image of a first property comprising at least a first structure, wherein the first structure is veiled in the first occluded image. Furthermore, the method includes a fourth step of feeding, at the damage classification system, the first occluded image to the generative model to generate a first reconstructed image in which the first structure is unveiled, and a fifth step of causing to be presented, at a computing device, the first reconstructed image.

In another aspect, a system for identifying property damage in occluded aerial imagery includes a processor and machine-readable media including instructions which, when executed by the processor, cause the processor to receive, at a damage classification system, first data including a first occluded image of a first property comprising at least a first structure, wherein the first structure is veiled in the first occluded image, and to feed, at the damage classification system, the first occluded image to a generative model to generate a first reconstructed image in which the first structure is unveiled. The instructions further cause the processor to extract, at the damage classification system, a first feature from the first reconstructed image, and to estimate, by the damage classification system, damage to the first property based on at least the first feature. In addition, the instructions cause the processor to classify, by the damage classification system, the first property depicted in the first reconstructed image under a damage category based on the estimated damage, and to cause to be presented, at a computing device, the damage category.

Other systems, methods, features, and advantages of the disclosure will be, or will become, apparent to one of ordinary skill in the art upon examination of the following figures and detailed description. It is intended that all such additional systems, methods, features, and advantages be included within this description and this summary, be within the scope of the disclosure, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DESCRIPTION OF THE EMBODIMENTS

The embodiments provide a system and method for automating the identification and inspection of buildings or other structures by making possible the use of occluded aerial imagery. As noted above, aerial imagery is often occluded by heavy smokes caused by wildfire, or by clouds that are often present for example, in the event of hurricane or tornado. Occlusions severely limit the ability of both automated and manually operated systems to detect damage to properties in image data. The disclosed embodiments employ a deep learning-based generative model with an autoencoder network architecture to reveal details in images that would otherwise be unusable. The model is trained on simulated occlusion images and restores the occluded images by performing an intelligent re-construction of the imaged site as it would have appeared without the occlusive features.

It can be appreciated that obtaining clear images during a disaster that present damage can expedite and simplify an otherwise onerous task. The proposed embodiments are designed to offer critical insights to insurance companies and other parties about specific structures that were damaged following a disaster, facilitating more accurate estimates of rebuilding costs and a more rapid turnaround for claim payouts to affected residents. In different embodiments, the systems described herein benefit from what could be considered an 'endless' supply of training data. The training data is created from clear (non-occluded) aerial images, which is available in plenty, by passing the normal images through a simulation engine to generate occluded images. In some embodiments, the simulation engine employs fractal expansion and chaos techniques to generate highly realistic occlusion. Both the clear images and their simulated occluded counterparts (image pairs) are inputted into the generative model as training data, and the model learns to recognize and discriminate patterns between the pairs. This process is fully automated and does not require manual labeling. The amount of training data inputted is thus capable of being immense, and is easily expanded, enabling development of a highly accurate generative model. Following training, the model is capable of receiving real (non-simulated) occluded images and generating a clarified image that can reveal structural details previously not apparent. In some embodiments, the system can then automatically determine a damage classification for the property. The proposed embodiments are designed to streamline settlements during disasters where the payout would otherwise be delayed as a result of damage estimate ambiguity stemming from occlusive aerial images.

Figure 1:
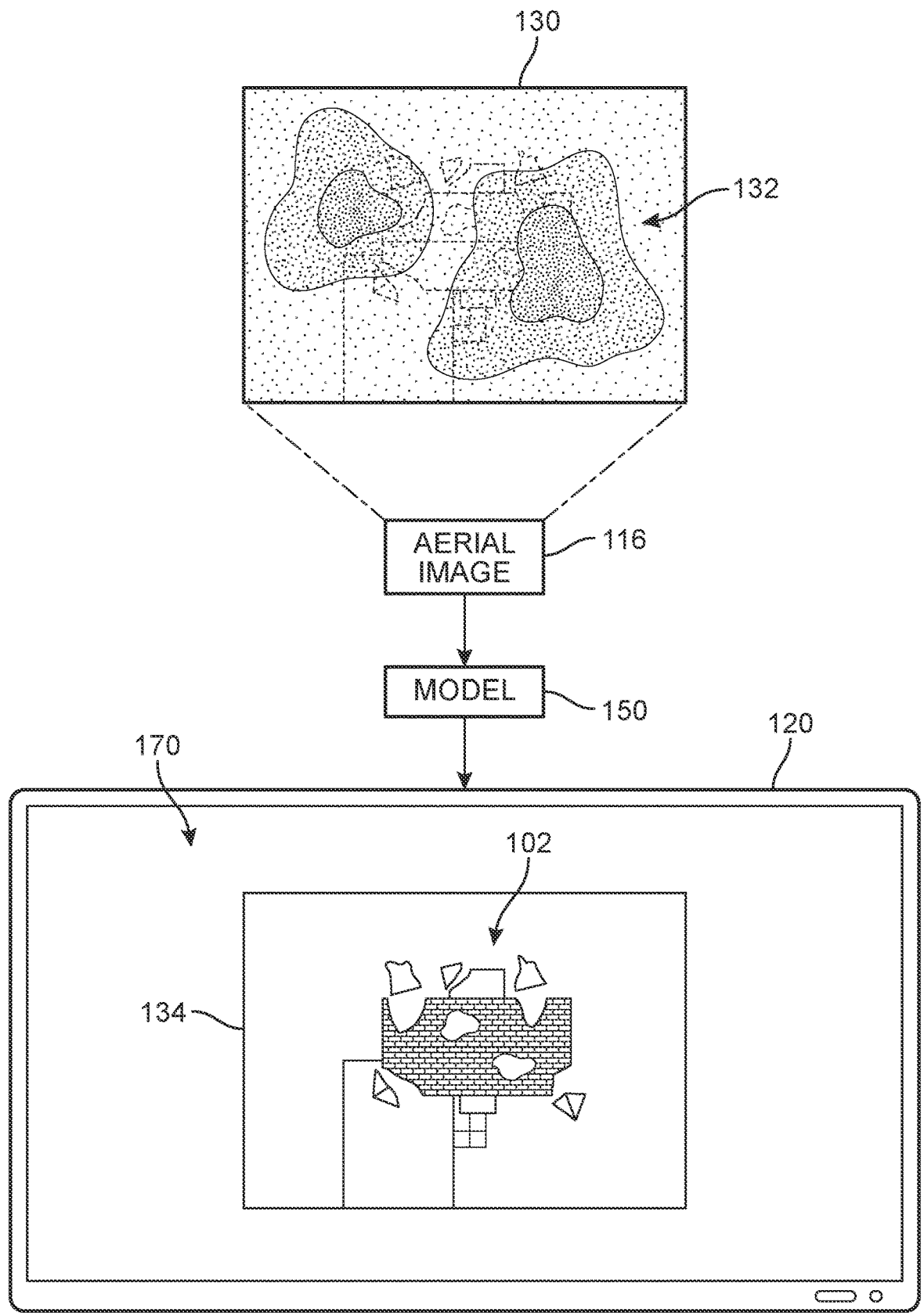
FIG. 1 is a schematic view of a generative model transforming a first occluded image to a clarified image, according to an embodiment.

For purposes of clarity, an overview of one embodiment of the proposed systems and methods is illustrated with reference to FIG. 1. In FIG. 1, an embodiment of a portion of a smart damage assessment system ("system") 100 implemented via a computing device 120 is depicted. In different embodiments, the system 100 is configured to receive aerial imagery-based image data 130 that may include occlusive features 132 (e.g., fog, smoke, rain, etc.) that obscure or obstruct views of structures in the images. Each image 116 is inputted to a trained generative model 150 that automatically removes or otherwise minimizes the occlusive features 132. In other words, the generative model 150 is configured to automatically simulate an image representation 134 of the site, for example in a display 170 for a computing device 120, that reveals the property captured in the image 116 with greater clarity. For purposes of this disclosure, references to occluded images refer to hazy image data including occlusive features of various modalities such as haze, smoke, rain, fog, low lighting, or other aspects that obstruct elements in the image, where the occlusive features block or otherwise hide or veil at least 5% of the property. In other words, occluded images offer limited details and low visibility. Structures that are present in an occluded image will be referred to as veiled structures. For example, a person viewing an occluded image would be unable to determine where most of the edges of a veiled structure are, or identify other structural characteristics such as (but not limited to) doorways, windows, roof tiles, sheds, or landscaping.

In different embodiments, the image representation 134 can reveal a building, such as a residence 102; in other words, the new image now presents what will be referred to as an unveiled structure. As used herein, the term "building" or "structure" can refer to any kind of building, such as a home, or other residential building, a shed, barn, a commercial building or any other related structures. A building typically can include a roof, room, walls, support structures, windows, or other features. The image representation 170 can refer generally to a visual reconstruction of the site or aspects thereof. In some embodiments, the image representation 170 can include additional details based on the type of image data used (e.g., RGB, infrared, etc.). An unveiled structure is a structure that was previously captured with little to no visibility in an aerial image, but is now visible with detail due to the simulated output of the generative model.

As shown in the example of FIG. 1, the residence 102 has been exposed to a natural disaster, and as a result was heavily damaged. In this case, the unveiled residence 102 can be seen to have suffered structural damage as well as exposure to fallen debris. In some embodiments, the system 100 may be configured to determine whether the damage detected is above a particular threshold, which can cause the property in the image to be classified as heavily damaged, catastrophically damaged, or a "total loss". If below that threshold, the property may be classified as to-be-determined (TBD), medium damage, light damage, or even no appreciable damage. In one embodiment, records for insured members that include pre-disaster imagery can be used as a reference when determining whether the current state of the structure, for example, whether the property now qualifies as a total loss. Furthermore, in some embodiments, the classification of a property as a total loss or another similar such label can cause the system to initiate an automated payout to the insured member.

Figure 2:
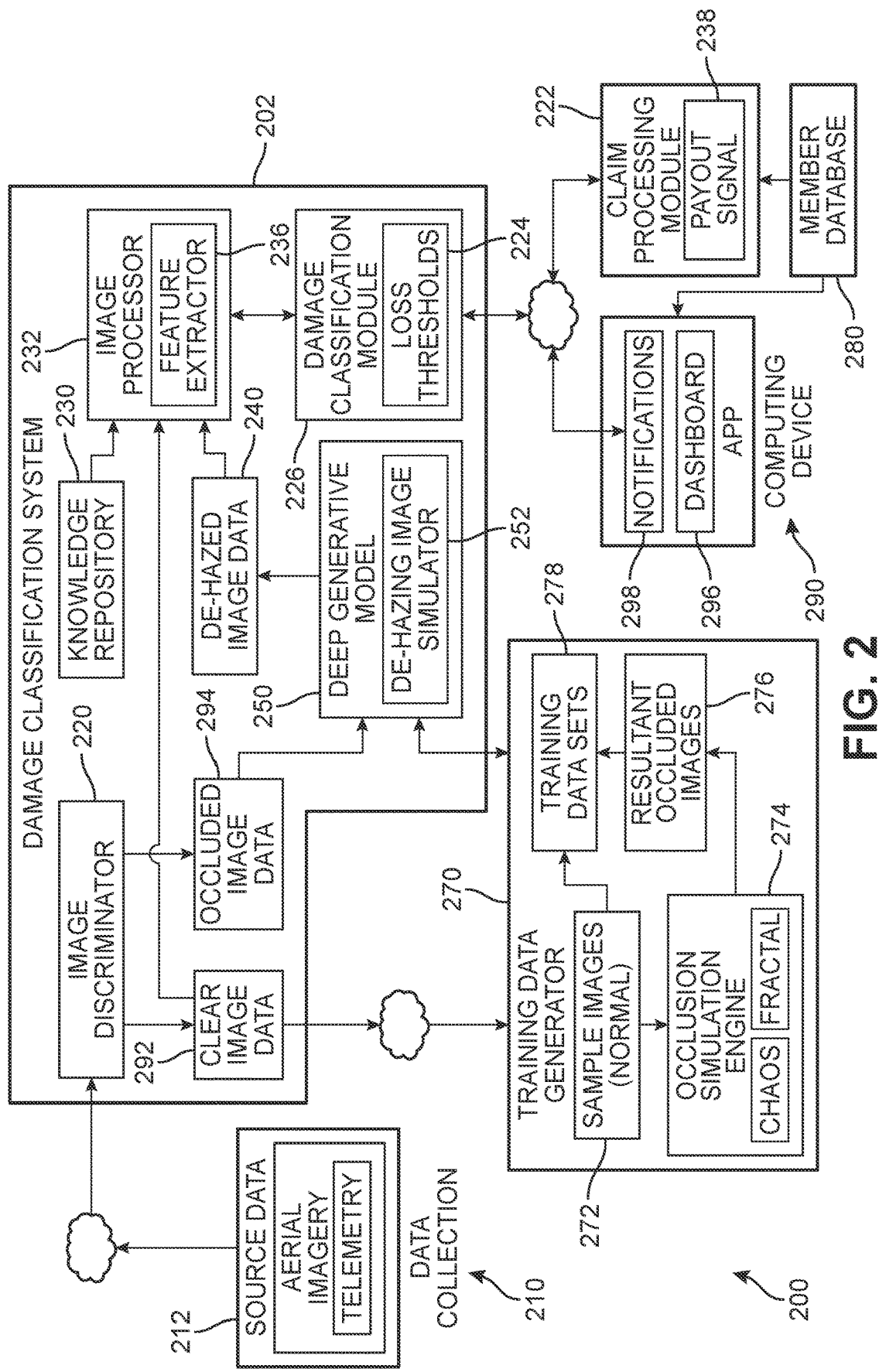
FIG. 2 is a schematic view of an architecture for a damage classification and training environment, according to an embodiment.

Referring now to FIG. 2, an overview of an embodiment of an architecture 200 for implementing the systems and methods disclosed herein is depicted. The architecture represents an environment for capturing and processing occluded images of structures covered by policies to improve the speed of assessing structural damage and facilitating claim processing following a disaster. In different embodiments, some of the steps may be performed by ground-based computing system(s) and some of the steps may be performed by aerial system(s). In FIG. 2 the cloud symbol refers to the use of a network to transmit or receive data.

In different embodiments, a data collection module 210 may represent an entry point whereby source data 212 may be received. In some embodiments, the source data 212 can be optionally stored in an image storage module for later reference and/or can be linked to the insured member's account for easy retrieval, and the data is accessed from the storage. In other embodiments, the image storage module is bypassed and source data 212 is directly inputted into a damage classification system ("system") 202. In different embodiments, some or all of the steps presented via FIG. 2 may be performed by components of cloud-based computing system(s) and some or all of the steps may be performed by components of local computing system(s). In other words, some or all components of the architecture 200 can be installed on a local computing device, or be accessed via a cloud server.

In different embodiments, the source data 212 itself may comprise various types of information, as discussed above. As some non-limiting examples, source data 212 can include aerial imagery 214 taken of various environments and structures, such as by drone, aircraft, satellite, etc. However, as described herein, in many cases lighting and other conditions can vary widely based on a variety of different factors, such as atmospheric haze, heat shimmer, seasonal variations, the amount of moisture, dust and smoke particles visible in the air (haze), which all contribute to visibility. A low haze layer can have a detrimental effect on image quality to the extent that, using conventional systems, little to no useful data (veiled structures) can be identified. For example, the introduction of smoke occluded vision introduces significant complications. Introduction of smoke severely degrades image quality thus affecting the number of usable features and extent of matching that can be performed. In addition, the presence of smoke in the environment loss of color contrast, precision and saturation, and the number of structural features that can be extracted decreases drastically as the camera moves into the haze areas.

In different embodiments, the aerial-based image data is of one or more structures or other points of interest located at a target site. The target site may include various structures, such as a residence or apartment building, a shed, barn, a commercial building or any other related structures. A building typically can include a roof, room, walls, support structures, windows, or other features. In some cases, the primary structure can be associated with additional secondary structures, features, or property that may be disposed adjacent to or otherwise near the primary structure. In some embodiments, the captured image data includes telemetry data 216 that is used to verify the location shown in the image, particularly useful in cases where the image is too occluded to even determine whether a structure is located at the site. For example, in some embodiments, the aerial image capture system can include an altitude and heading reference system (AHRS) based on which the orientation, heading, and height of the aerial vehicle and any camera can be determined. This information, when used with a GPS location for the aerial vehicle, can be used to infer the location of one or more points in an image taken from the aerial vehicle.

Source data 212 is received by system 202 at an image discriminator module 220. In some embodiments, machine vision, image recognition, and/or related analysis can be used to identify elements of source data 212. In different embodiments, the image discriminator module 220 may differentiate between clear image data 292 that offer visibility with respect to the site and occluded image data 294 in which details are difficult to discern. In some embodiments, clear image data 292 can be shared with a training data generator 270, as well as directly to an image processor 232 for further analysis, thereby bypassing the de-hazing process. The occluded image data 292 is received by a deep generative model 250 which has been trained to receive image data inputs and transform or otherwise reconstruct a simulated 'de-hazed' image via de-hazing image simulation engine 252. Generally, the process of enhancing, transforming, and/or reconstructing an image occluded by smoke/fog/haze is commonly referred to as image de-hazing, and in this case the term is used to refer to the process of employing deep generative model 250 to develop new images where the haze or other occlusive features have been removed to reveal structural or other property details.

Figure 3:
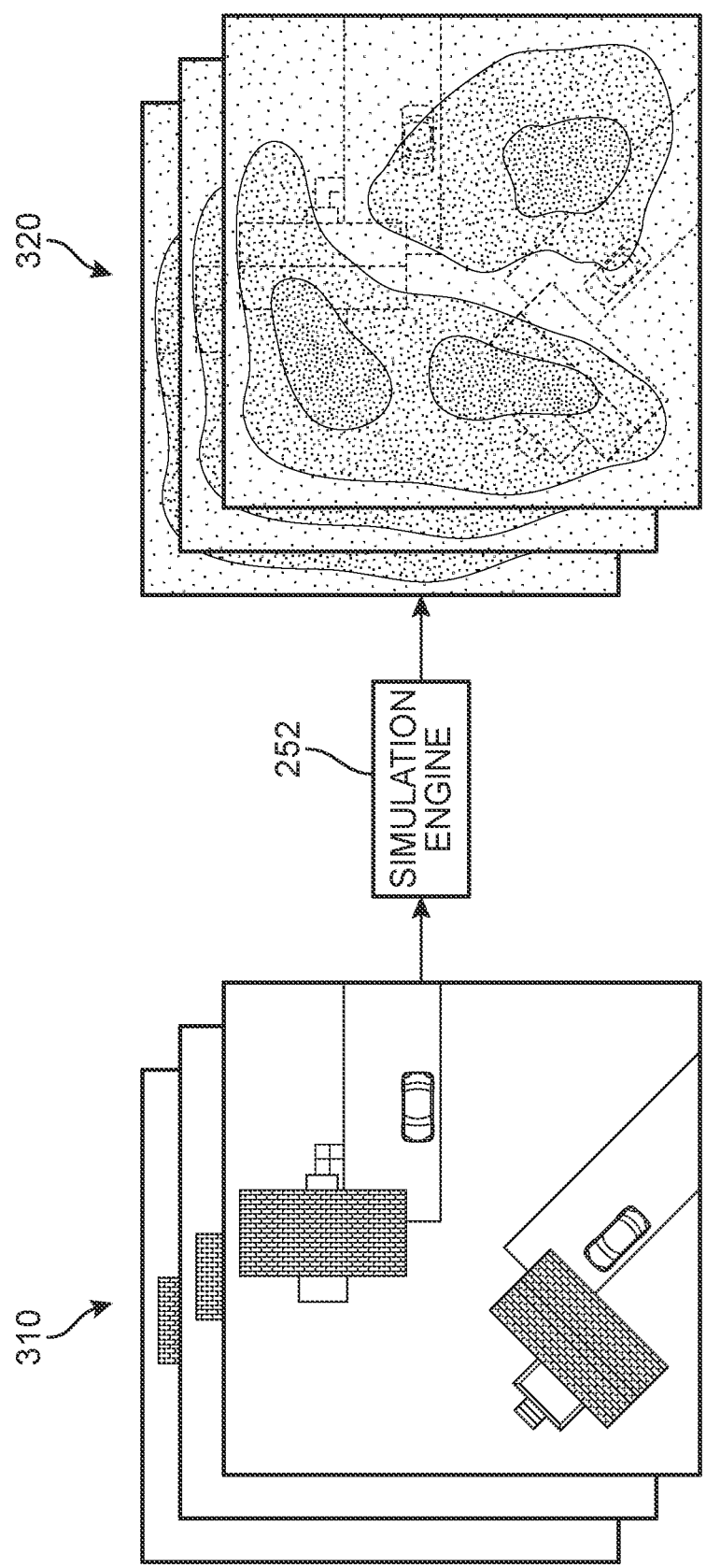
FIG. 3 is an example of a simulation engine generating training data for the generative model, according to an embodiment.

In other words, deep generative model 250 is configured to produce a high-visibility reconstruction simulation ("simulation") of each occluded image as de-hazed image data 240. In different embodiments, the simulation can vary widely in detail, depending on the quality and quantity of source data 212. In some embodiments, deep generative model 250 applies one or more of generative multi adversarial nets (GMAN) and conditional generative adversarial nets (CGAN), as well as other image synthesis techniques in generative adversarial networks (GAN). As a general matter, generative modeling involves using a model to generate new examples that plausibly come from an existing distribution of samples, such as generating new photographs that are similar but specifically different from a dataset of existing photographs. Thus, in this case, the deep generative model 250 can be trained with sample pairs of clear and occluded images of the same location. In other words, each pair will comprise identical images except one will be occluded and the other will have increased visual perception and clarity for increasing structural feature extraction. One example of this process is depicted in FIG. 3, where a set of normal-visibility (clear) images 310 are inputted into the simulation engine 252. The output is a set of occluded or low visibility images 320, which are each linked to their original normal image to produce a training data pair.

As shown in FIG. 2, training data generator 270 can receive a volume of sample aerial images ("sample") 272 of various target sites with good visibility and employ an occlusion simulation engine 274 to transform each image of the sample 272 to the same images with diminished visibility, referred to as resultant occluded images 276. These pairs (training data sets 278) are then received by the deep generative model 250 in order to simulate the type of image data that will be received as occluded image data 294 and teach the model to recognize how the same images when de-occluded would appear. In different embodiments, the occlusion simulation engine 274 applies chaos and/or fractal expansion theory-based techniques to produce the occlusion effects.

In different embodiments, the occlusion simulation engine 274 reduces the dynamic range of the pixel intensities of the image, from the full intensity scale to a randomly compressed intensity scale to create an occluded or corrupted image in one pass. This output will train the generative model. In addition, occlusive features such as realistic cloud and smoke are simulated based on fractal and chaos theories, causing the image to be degraded through random process, rather than a uniform change. For purposes of reference, in one embodiment, the following code can be used to generate the resultant occluded images 276 based on sample 272:

```
import os, glob
from imageio
import imread,
imsaveimport
matplotlib.pyplot
as plt import
tqdm
fnames=glob.glob('../data/fire-dmg/TRAIN/*/*.jpg')
  fnames.sort( )
len(fnames)
for i, fname in enumerate(fnames[:5]):
  try:
    img=imread(fname)
  except:
    continue
  fig, axes=plt.subplots(1, 2,
  figsize=(18, 9))
  axes[0].imshow(img)
  mi=0.1+
  (np.random.rand( )-
  0.5)/5ma=mi+
  np.random.rand( )/2
  print(i, (mi, ma))
  out=(np.interp(img, (0, 255), (mi, ma))*255).astype
    (np.uint8)
  axes[1].imshow(out)
  plt.show( )
out.shape, out.dtype
good_dir='good_input'
bad_dir='bad_input-1'
os.makedirs(good_dir, exist_ok=True)
os.makedirs(bad_dir, exist_ok=True)
i=0
for fname in tqdm.tqdm(fnames):
  try
    img=imread(fname)
  except:
    continue
  for j in range(3):
    mi=0.1+(np.random.rand( )-0.5)/5
    ma=mi+0.05+np.random.rand( )/5
    #print(i, (mi, ma))
    out=(np.interp(img, (0, 255), (mi, ma))*255).astype
      (np.uint8)
    imsave(os.path.join(good_dir, '%05d.jpg' % i), img,
      quality=98)
    imsave(os.path.join(bad_dir, '%05d.jpg' % i), out,
      quality=98)
    i+=1
```

Once the deep generative model 250 has been trained, occluded image data 294 can be inputted. The model 250 output is used by de-hazing simulation engine 252 to create a reconstruction in which the features are clarified. An embodiment of a code that performs the reconstruction is as follows:

```
% reload_ext au oad
% autoreload 2%
matplotlib inline
from fastai import *
from fastai.vision import *
from fastai.callbacks.hooks import *
def n(x):
  return Path(str(x). replace('bad_input-1/', 'good_
    input/'))
src=(ist.from_folder('bad_input-1')
  .split_by_rand_pct( )
  .label_from_func(get_y_fn))
sz=224
bs=64
tfms=get_transforms(flip_vert=True, max_lighting=0.1,
    max_zoom=1.05,
max_warp=0.)
data=(src.transform(tfms, size=sz, tfm_y=True)
  .databunch(bs=bs)
  .normalize(imagenet_stats))
data.c
data.device
data.show_batch(rows=5)
learn=unet_learner(data, models.resnet34,
    loss_func=MSELossFlat( ), wd=1e-3)
learn.lr_find( )
learn.recorder.plot( )
lr=3e-3
learn.fit_one_cycle(10, slice(lr, pct_start=0.9)
learn.save('dra_unet34-stage1')
learn.recorder.plot_losses( )
learn.unfreeze( )
lrs=slice(lr/400, lr/4)
learn.fit_one_cycle(12, lrs, pc 0.8)
learn.save('dra_unet34-stage2')
learn.recorder.plot_losses( )
learn.show_results(rows=5)
learn.export('dra_unet34')
```

In some embodiments, the de-hazed image data 240 is received by image processor 232 that includes an image recognition processor that can, for example, apply a convolutional neural network. In another example, computer learning may be used to recognize image elements such as structures, vehicle parts, persons, environmental features, etc. In some embodiments, a knowledge repository 230 can include information about the specific features that are relevant to the damage classifier, such as indications of water damage, flooding, and/or downed power lines and broken structures. The image processor 230 may use GPS data or other geolocation data to tag the image.

In some embodiments, the computing device may recognize one or more positions or features in the image data, such as based on shapes, patterns, or colors of the image data and identify such via feature extractor 236. As another illustrative example, the system may recognize a feature of a vehicle, such as a roof, a trunk, or a door, for example. The system may be taught to recognize features or positions by a machine learning algorithm trained with disaster-specific data obtained from knowledge repository 230.

In different embodiments, once the de-hazed image data 240 is generated, it may be presented to a user of a computing device 290 to facilitate review of the disaster site, for example via a user interface such as a dashboard 296. As a general matter, an "interface" may be understood to refer to a mechanism for communicating content through a client application to an application user. In some examples, interfaces may include pop-up windows that may be presented to a user via native application user interfaces (UIs), controls, actuatable interfaces, interactive buttons or other objects that may be shown to a user through native application UIs, as well as mechanisms that are native to a particular application for presenting associated content with those native controls. In addition, the terms "actuation" or "actuation event" refers to an event (or specific sequence of events) associated with a particular input or use of an application via an interface, which can trigger a change in the display of the application.

Furthermore, a "native control" refers to a mechanism for communicating content through a client application to an application user. For example, native controls may include actuatable or selectable options or "buttons" that may be presented to a user via native application UIs, touch-screen access points, menus items, or other objects that may be shown to a user through native application UIs, segments of a larger interface, as well as mechanisms that are native to a particular application for presenting associated content with those native controls. Voice control can also be used to actuate options. The term "asset" refers to content that may be presented in association with a native control in a native application. As some non-limiting examples, an asset may include text in an actuatable pop-up window, audio associated with the interactive click of a button or other native application object, video associated with a teaching user interface, or other such information presentation.

In some embodiments, the simulation may be transmitted from a remote server where some or all components of the system reside. In some cases, the user could be a representative, such as for an insurance company that provides coverage for the property. In some cases, upon receiving the simulated image data, the representative could call the claimant to review the image and gather any additional relevant information or clarifying details. In some embodiments, the simulation could be sent to other parties. As one example, the simulation could be sent to a repair facility to provide a visual image of the type of damage that will need to be repaired. This process of reviewing a simulation of a site that no longer is occluded may provide expedited servicing of claims over alternative methods that rely on manual visits or images captured after the occluding features have dissipated.

In other embodiments, the processed image data and extracted features could be automatically analyzed to retrieve relevant analytic data without the need for a manual review, via a damage classification module 224. The damage classification module 224 can refer to pre-established thresholds 224 based on the extracted features and degree of damage detected. For example, a house without a roof may be determined to represent a total loss, and a house with a roof with debris may be a high-level loss, while a house with debris scattered nearby but otherwise intact may be a low-level loss or no loss. In some embodiments, the classification can also be based on the insurance policy of the member, which may delineate the levels of damage that should lead to a claim payout. Each image—or in some cases, group of images of the same site—is processed, the damage classification module 226 determines what loss level should be assigned to the property detected in the imagery. In some embodiments, the outcome can be presented at the dashboard 296 and/or via a notification 298 (e-mail, chat message, pop-up, etc.) at the computing device 290. In another embodiment, a claim processing module 222 is configured to receive the outcome data and determine whether, based on the system settings, member's records, member's preferences, and terms of the member's policy currently in force, the insured property has sustained a high enough level of damage so as to trigger an automated payout. For example, a payout signal 238 can be generated to cause the release of a pre-set amount of funds from a financial account to the member's bank or other account. In other words, in cases where the damage classification module 226 assigns a damage class to the property greater than a given threshold, the claim processing module 222 can automatically generate a preliminary claim for that property based on the classification. This claim is then immediately processed for payout and allows affected members to have expedited access to funds in times of emergency.

Figure 4:
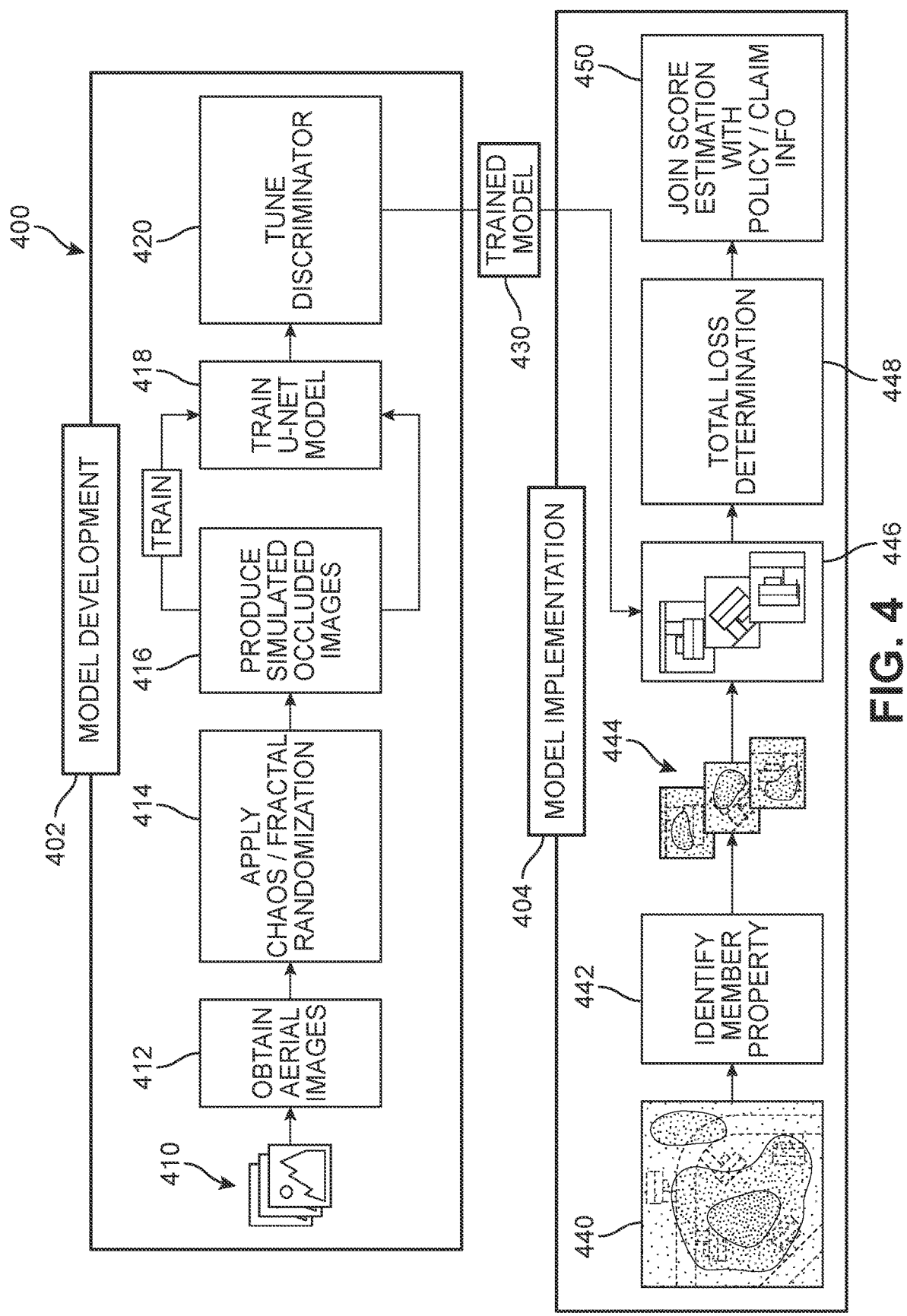
FIG. 4 is a high-level flow diagram of a model development and implementation, according to an embodiment.

In different embodiments, the system can include provisions for generating highly accurate damage classifications using occluded imagery. In FIG. 4, one embodiment of a flow process 400 for development and implementation of a machine learning model for image processing is shown. The flow process 400 includes a first stage 402 (model development) and a second stage 404 (model implementation). During the first stage 402, input 410 in the form of sample imagery is provided to the system. The input 410 is cleansed and normalized in a first step 412 using various image processing algorithms and/or software that may be used with captured image data. In one embodiment, the image processing algorithms perform compression, artifact correction, noise reduction, color corrections, geometric corrections, imager non-uniformity correction, etc., and various image processing enhancement operations on the image content. The algorithms can be implemented as software running on a processor, DSP processor, special purpose ASIC and/or FGPA's. The image processing algorithms can also be a mixture of custom developed algorithms and libraries. The image processing algorithms can further be arranged in any logical sequence, with potential changes in the sequence of processing or parameters governing the processing determined by image type, computational requirements or outputs from other algorithms.

In some embodiments, image processing may also include machine learning techniques that can be used to discriminate between features and to identify objects, for example via image recognition and object detection software. Such techniques may also include machine vision algorithms that perform, among other operations, symbol and logo recognition, general shape recognition, as well as object classification. The machine vision algorithms may reside on a different system belonging to a different entity than the image processing algorithms or the application software. The machine vision algorithms, which are applied to identify an object in the digital image, may include computer vision algorithms such as image analysis algorithms that may use a feature detector or a combination of detectors. For example, texture detectors and edge detectors known to those skilled in the art may be used. If both specific texture and specific edges are detected in a set of images, then an identification may be made. One non-limiting example of an edge detection method includes the Canny™ algorithm available in computer vision libraries such as Intel™ OpenCV. Texture detectors may use known algorithms such as texture detection algorithms provided by Matlab™. Some non-limiting examples of object detection algorithms include R-CNN, SPP, Fast R-CNN, Faster R-CNN, Feature Pyramid networks, RetinaNet (Focal loss), Yolo Framework—Yolo1, Yolo2, Yolo3, and SSD.

The images are then occluded in a second step 414, as discussed in FIG. 2 to produce simulated occluded images in a third step 416. The model is trained and validated in a fourth step 418. In different embodiments, the model can include a neural network (e.g., CNN, RNN, UNet, etc.) that is trained and tuned based on the output of third step 416. More specifically, machine learning techniques, such as deep learning that includes classification, clustering, and/or other techniques, are applied to the dataset to develop the model(s). Such ML techniques may include, but are not limited to, techniques that employ deep learning neural networks for pattern recognition within the image data, or to perform other types of analysis. For example, a neural network and/or classification technique may be used to train a model that is a classifier and that is useable to detect different types of damage. Some suitable artificial intelligence software is available for public access through open-source AI platforms like Caffe, Torch and Theano who provide businesses access to powerful neural networks for processing of their information by AI techniques like deep learning, reinforcement learning and logistic regression, as well as TensorFlow, OpenAI, and BigSur. All of these AI systems process enormous amounts of data; for example, Caffe can process over 60 million images per day with a single NVIDIA K40 GPU.

Once a model has been trained, the model can be further tuned or adjusted to fit the intended deployment environment in a fifth step 420, and the resulting trained generative model 430 is delivered to the model implementation stage 404. In a sixth step 442, aerial image data 440 with occluded properties are obtained, and information for the individual member property can be accessed. The image data 440 is provided to the trained generative model 430, which generates reconstructed simulation imagery 446 which represents the imagery with the occlusive features removed. In a seventh step 448 the generated images are received by the damage classifier and a score is assigned describing the level of loss. For example, the selected classification can be applied for a structure according to various levels of damage. As an example, the damage classification model could assess structures as having "no damage," "minor damage," "significant damage," or "total loss", or across a more extensive metric, such as an assignment of a number (e.g., between 0 and 10, 0 and 50, 0 and 100, or any other range) in which zero represents no damage and the maximum number represents catastrophic damage. Of course, other classifications are possible. In addition to classifying the structures according to levels of damage, a damage classifier could also classify the amount of damage using other metrics such as the cost of damage, the cost of payout, as well as other possible metrics. The obtained estimated score or classification is linked to the member's policy and claim information in an eighth step 448, which can then be shared with the insurance agents or used to cause an automated payout.

Figure 5:
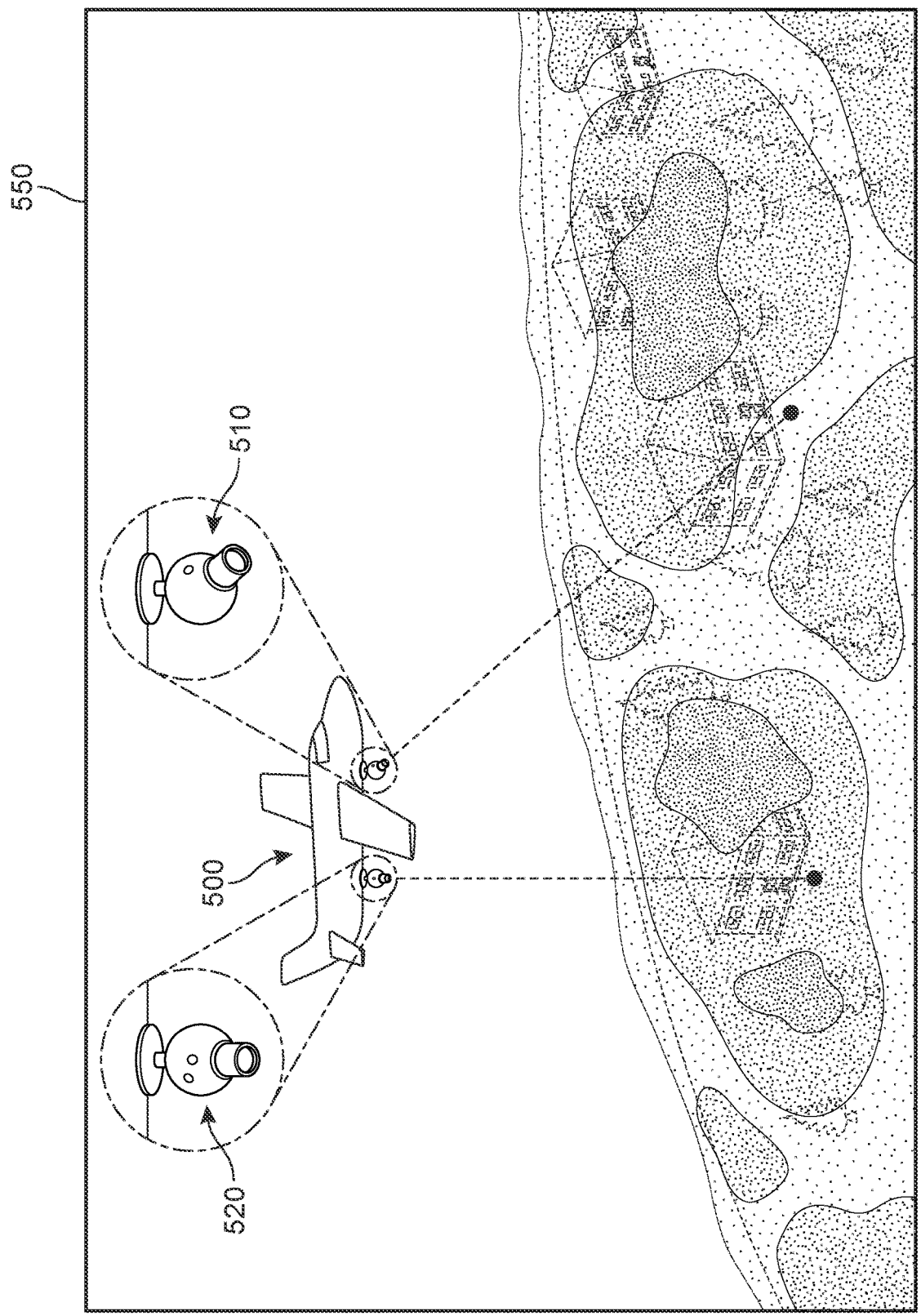
FIG. 5 is an illustration depicting an aerial vehicle capturing images of a first location following a natural disaster, according to an embodiment.
Figure 6:
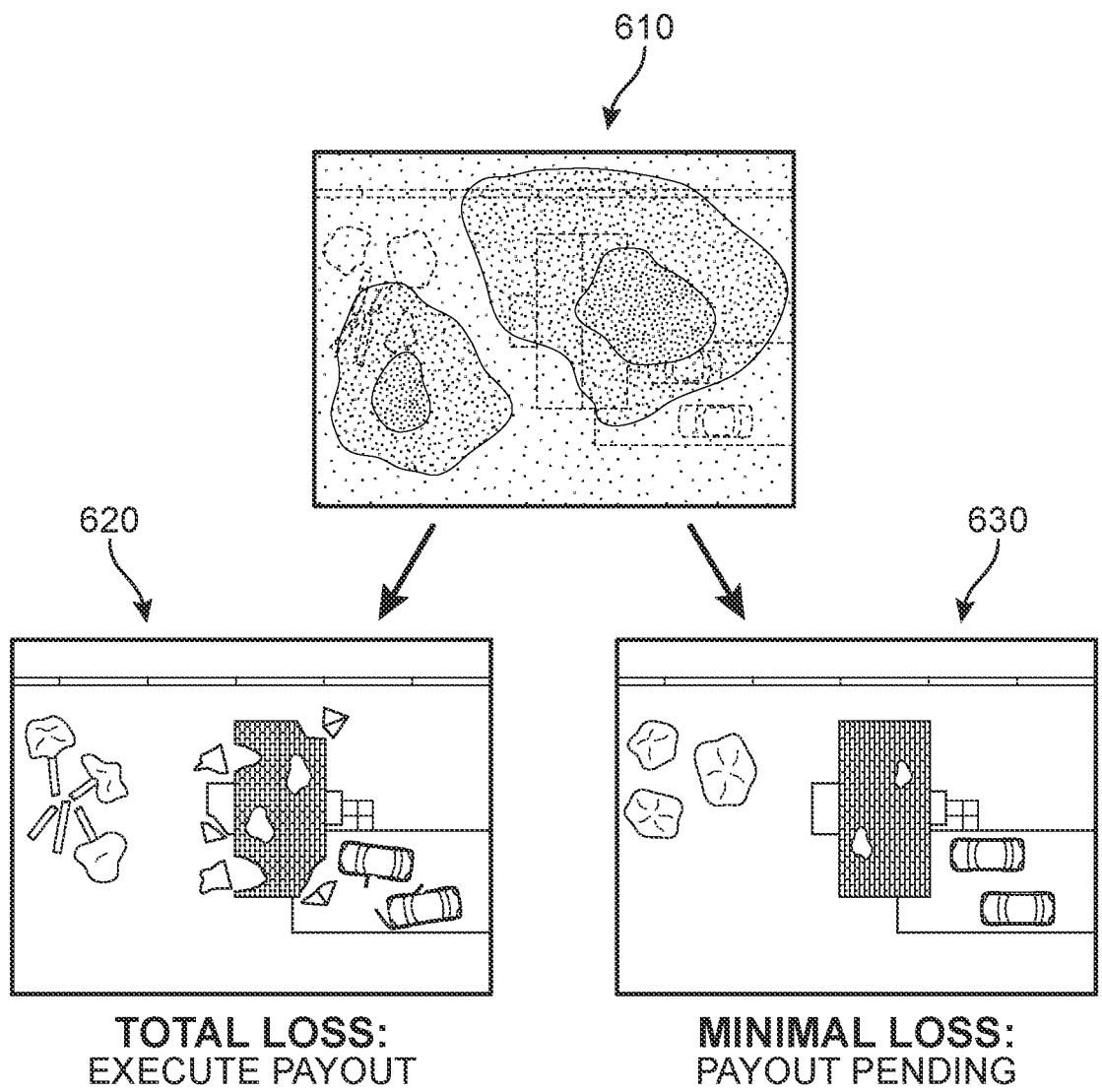
FIG. 6 is an example of two possible claim processing outcomes based on an occluded image according to an embodiment.
Figure 7:
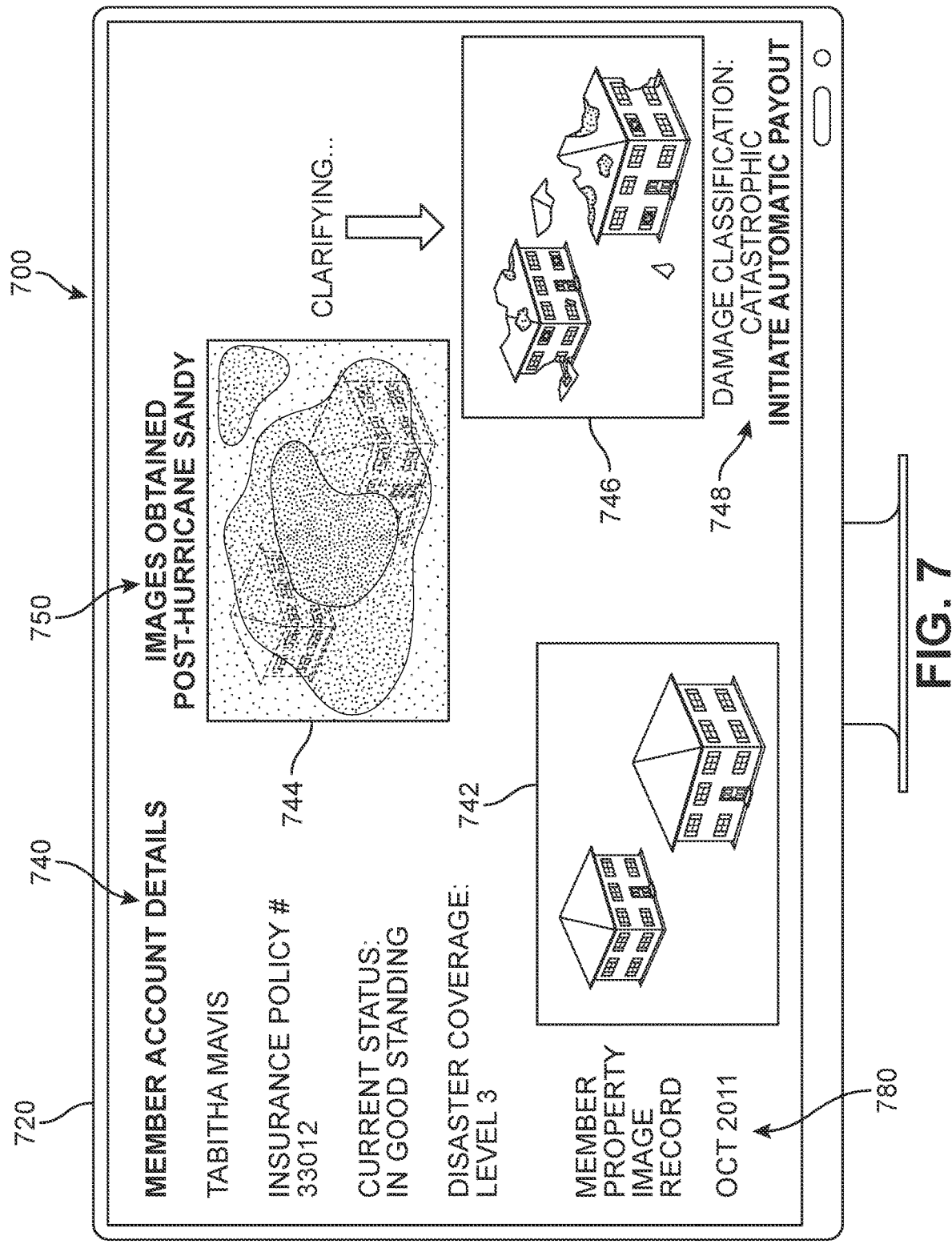
FIG. 7 is an example of a user dashboard presenting information about a damaged structure based on an occluded image, according to an embodiment.

Referring to FIGS. 5-7, a sequence of drawings depicts one example scenario in which the proposed systems can be implemented. In FIG. 5, an aerial vehicle 500 with camera 510 and 520 is flying over an extremely low-visibility region 450. In this case, very little detail can be seen due to the haze effect caused by smoke. In FIG. 6, an occluded image 610 is reconstructed. For purposes of illustration, it can be understood that the occluded image 610 is so hazy that it would have been difficult to determine whether a first view 620 or a second view 630 was accurate. In the first view 620, the roof of a house has been substantially damaged, and debris is strewn nearby. In contrast, the second view 630 presents the house as mostly unaffected by any external conditions. An insurance company will not be able to make claim decisions based on such hazy data. However, for the affected residents, the ability for insurance companies to accurately determine whether help is required is of paramount importance. A system that can clarify occluded images as described herein can offer victims of disasters a chance to recover more quickly even when environmental conditions have made imagery of their surrounding area occluded.

In different embodiments, the system can generate such information and provide an end-user with a variety of interactive tools to monitor and manage the damage data. As one non-limiting example, FIG. 7 depicts a user dashboard 750 that can be presented to end-users to quickly convey information and observations about properties in a region. The dashboard 750 in FIG. 7 is shown on a display 720 of a computing device 700, and is configured to offer a wide range of information, including analytics overview for the region in which the insured residence is located, details regarding the disaster event, and metrics that can present a pictorial summary of various aspects of the processed data.

In different embodiments, the display 720 of computing device 700 may present information and various media for a product/service support software application ("app"). In some embodiments, the app is associated with the provider of the product/service for which the end-user is employed. In some embodiments, the end-user can receive and send information through a user interface that may be presented on a display for the device. In some embodiments, the display may be a touchscreen, allowing the end-user to interact with the user interface directly by touch. The user interface may refer to an operating system user interface or the interface of one or more software applications that may run on the computing device 700. In some embodiments, the user interface can include a messaging window or other chat-space by which the employee/agent may send messages or other digital content. In different embodiments, the computing device 700 is part of or in communication with a computing system which provides access to the damage classification system 202 of FIG. 2.

The term "computer system" refers to the computing resources of a single computer, the partial computing resources of a single computer, a plurality of computers communicating with one another, or a network of remote servers. In one embodiment, computer system includes at least one server having at least one processor. In different embodiments, the computer system includes one or more computing devices (for example, a server) that may be in communication with one or more databases. Databases could be co-located with computing devices or could be remote databases that are accessible by computing devices over a network. Databases can include any kind of storage devices, including but not limited magnetic, optical, magneto-optical, and/or memory, including volatile memory and non-volatile memory. In an example embodiment, the computer system may also include or be configured with access to a damage classification system 202, training data generator 270, and other components of the architecture 200 of FIG. 2.

In different embodiments, computing devices 120, 290, and 700 can include an electronics unit comprising a plurality of different components, such as a user interface component (e.g., a touchscreen display, keyboard, mouse, microphone, etc.), a sensor unit (including one or more cameras or other image-based sensors), a user interface module, a processor, and/or a communication module. Furthermore, the computing devices may also include or be connected to a microphone and speaker. The computing devices may include a system including one or more processors and memory. Memory may comprise a non-transitory computer readable medium. Instructions stored within memory may be executed by the one or more processors.

A communication module may allow the computing devices to communicate wirelessly, for example via a network. However, wired connections may also be used. For example, the communication module may include a wired serial bus such as a universal serial bus or a parallel bus, among other connections. The communication module may also include a wireless connection using Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities.

In one embodiment, computing devices could operate in a client-server relationship with one or more servers of computer system for the damage classification system. For example, the computer system may include a server that communicates with computing devices, as well as other remote devices (e.g., user devices of other customers) over a network. The computing devices may provide the front-end of a system that provides users with options for performing various kinds of tasks (for example, making fund transfers when the company is a bank). In some cases, computing devices may run client software through a web browser, in which case the client software may be hosted on a server associated with the authentication computer system. In other cases, computing devices may run client software in the form of a native software application that has been downloaded through a centralized marketplace (i.e., an "app store"). In some cases, while the client software that allows users to perform various tasks may be run on computing devices, the data may be retrieved from and stored on databases associated with authentication computer system (e.g., databases).

In other embodiments, the system can present various metrics and reports for individual structures as well as for larger groups of structures in a region. In some embodiments, some or all of these reports can be presented in graphical form, such as images, bar graphs, line graphs, pie charts, cartesian graphs, percent complete indicators, etc. In this case, account information 740 for an insured member "Tabitha Mavis" has been accessed, and policy information is shown. In some embodiments, the account information 740 can include a previously captured (pre-disaster) image that is stored as a member record 742. When a disaster occurs, the system described above can obtain updated aerial imagery as first member property image 744. As shown in FIG. 7, the first member property image 744 is hazy and does not indicate the impact the disaster may have had on the property. The first member property image 744 is submitted to the damage classification system and a simulated second member property image 746 is generated in which the damage is clear. The damage classifier assigns a label to the property ("catastrophic"), which is presented on the display 720 as a notification 748. In some embodiments, the damage level can exceed a damage threshold, and cause an automatic payout to be triggered. In some embodiments, the payout can be modulated based on the degree of damage that was detected by the classifier (e.g., higher damage scores lead to larger payouts, smaller damage scores lead to smaller payouts).

It should be understood that the dashboard 750 of FIG. 7 represents only one possible depiction of interfaces that may be offered to the end-user, and in other embodiments, any variation in presentation style, options, menus, and graphical depictions can be used, including interfaces customized by the end-user to display the desired information. A Settings option can also be displayed to allow the end-user to create or modify the account. In addition, a number of interface layer options may be provided. For example, other options can allow the user to switch to a landing page that presents a brief summary of the user's account or a log of the user's previous activity.

Figure 8:
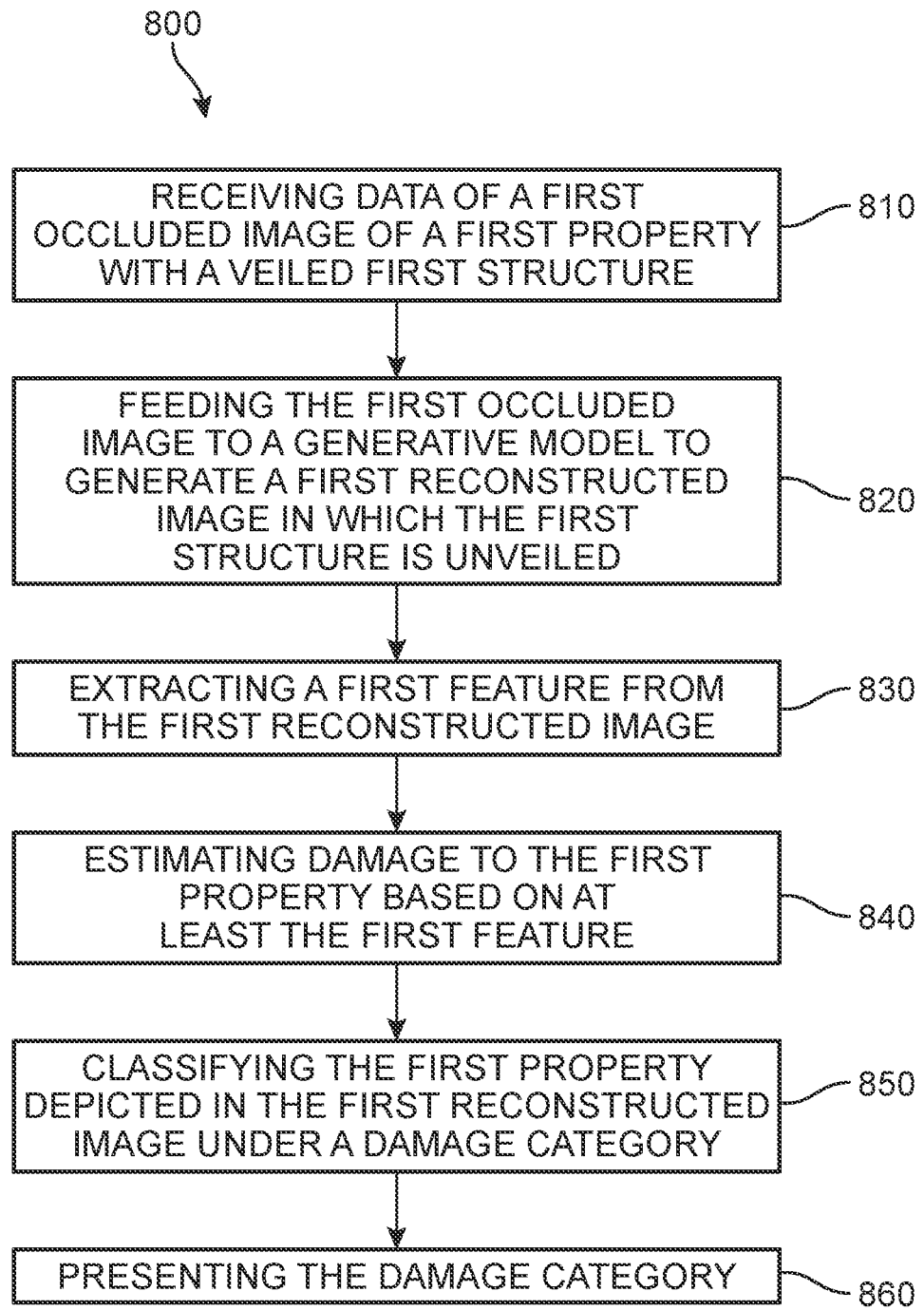
FIG. 8 a flow chart depicting a process of identifying property damage in occluded aerial imagery, according to an embodiment.

FIG. 8 is a flow chart illustrating an embodiment of a method 800 of identifying property damage in occluded aerial imagery. The method 800 includes a first step 810 of receiving, at a damage classification system, first data including a first occluded image of a first property comprising at least a first structure, wherein the first structure is veiled in the first occluded image, and a second step 820 of feeding, at the damage classification system, the first occluded image to a generative model to generate a first reconstructed image in which the first structure is unveiled. The method 800 also includes a third step 830 of extracting, at the damage classification system, a first feature from the first reconstructed image, and a fourth step 840 of estimating, by the damage classification system, damage to the first property based on at least the first feature. A fifth step 850 includes classifying, by the damage classification system, the first property depicted in the first reconstructed image under a damage category based on the estimated damage, and a sixth step 860 includes causing to be presented, at a computing device, the damage category. At least a portion of the method is performed by a processing unit.

In other embodiments, the method 800 may include additional steps or aspects. In one embodiment, the method 800 also includes steps of receiving, at the damage classification system, a training dataset, the training dataset comprising pairs of images, each pair including a first image and a second image, the first image providing a high visibility picture of a property, the second image providing a low visibility picture of the same property in the same position as in the first image, and training, at the damage classification system, the generative model using the training dataset to produce high visibility pictures from occluded imagery. In some embodiments, the second image is created employing an occlusion simulation engine that uses fractal expansion theory to add occlusive features to the first image. In another embodiment, the method 800 also includes a step of employing, at the damage classification system, a machine learning model to detect damage to the first structure in the first reconstructed image.

In different embodiments, the method 800 can also include steps of generating, at the damage classification system, a damage score for the first property based on the first reconstructed image, and selecting, at the damage classification system, the damage category based on the damage score. In another example, the damage score is greater than a pre-set damage threshold. In such cases, the method 800 can also include steps of generating, at the damage classification system, an output indicating the damage score is above the threshold, transmitting, from the damage classification system, the output to a claims processing module, and causing, at the claims processing module and in response to the output, a payout signal to be generated that is configured to automatically release funds to a beneficiary of an insurance policy for the first property. In one example, the method 800 further includes steps of generating, at the damage classification system, an output describing the damage to the first property, transmitting, from the damage classification system, the output to a claims processing module, and causing, at the claims processing module and in response to the output, a preliminary claim to be generated that is configured to expedite a payout to a beneficiary of an insurance policy for the first property.

Other methods may be contemplated within the scope of the present disclosure. For example, in some embodiments, a method of clarifying occluded images to determine property damage is disclosed. The method includes a first step of receiving, at a damage classification system, a training dataset, the training dataset comprising pairs of images, each pair including a first image and a second image, the first image providing a high visibility picture of a property, the second image providing a low visibility picture of the same property in the same position as in the first image. A second step includes training, at the damage classification system, a generative model using the training dataset to produce high visibility pictures from occluded imagery. The method also includes a third step of receiving, at the damage classification system, first data including a first occluded image of a first property comprising at least a first structure, wherein the first structure is veiled in the first occluded image. Furthermore, the method includes a fourth step of feeding, at the damage classification system, the first occluded image to the generative model to generate a first reconstructed image in which the first structure is unveiled, and a fifth step of causing to be presented, at a computing device, the first reconstructed image.

In other embodiments, this method may include additional steps or aspects. In some embodiments, the first data further includes a location of the first property, and the method further comprises causing to be presented, at the computing device, the first occluded image and information about an account associated with the location. In one embodiment, the method may also include steps of extracting, at the damage classification system, a first feature from the first reconstructed image, and estimating, by the damage classification system, damage to the first property based on at least the first feature. In one example, the method can also include a step of classifying, by the damage classification system, the first property depicted in the first reconstructed image under a damage category based on the estimated damage. In another example, the method further includes a step of causing to be presented, at the computing device, the damage category. In some embodiments, the method additionally includes steps of generating, at the damage classification system, an output describing the estimated damage to the first property, transmitting, from the damage classification system, the output to a claims processing module, and causing, at the claims processing module and in response to the output, a preliminary claim to be generated that is configured to expedite a payout to an owner of the first property.

Media generated applying one or more of the techniques disclosed herein may be displayed on a monitor or other display device. In some embodiments, the display device may be coupled directly to the system or processor generating or rendering the images. In other embodiments, the display device may be coupled indirectly to the system or processor such as via a network. Examples of such networks include the Internet, mobile telecommunications networks, a WIFI network, as well as any other wired and/or wireless networking system. When the display device is indirectly coupled, the images generated by the system or processor may be streamed over the network to the display device. Such streaming allows, for example, video games or other applications, which render images, to be executed on a server or in a data center and the rendered images to be transmitted and displayed on one or more user devices (such as a computer, video game console, smartphone, other mobile device, etc.) that are physically separate from the server or data center.

In addition, sound or other audio generated applying one or more of the techniques disclosed herein may be produced by a speaker or other audio output device. In some embodiments, the audio device may be coupled directly to the system or processor generating the sound. In other embodiments, the audio device may be coupled indirectly to the system or processor such as via a network. Examples of such networks include the Internet, mobile telecommunications networks, a WIFI network, as well as any other wired and/or wireless networking system. When the audio device is indirectly coupled, the sound generated by the system or processor may be streamed over the network to the display device. Such streaming allows applications and other software which include audio to be executed on a server or in a data center and the generated sound to be transmitted and produced by one or more user devices (such as a computer, smartwatch, smartphone, other mobile device, etc.) that are physically separate from the server or data center. Hence, the techniques disclosed herein can be applied to enhance the sounds that are streamed and to enhance services that provide audio.

The processes and methods of the embodiments described in this detailed description and shown in the figures can be implemented using any kind of computing system having one or more central processing units (CPUs) and/or graphics processing units (GPUs). The processes and methods of the embodiments could also be implemented using special purpose circuitry such as an application specific integrated circuit (ASIC). The processes and methods of the embodiments may also be implemented on computing systems including read only memory (ROM) and/or random access memory (RAM), which may be connected to one or more processing units. Examples of computing systems and devices include, but are not limited to: servers, cellular phones, smart phones, tablet computers, notebook computers, smart watches, smart glasses, e-book readers, laptop or desktop computers, all-in-one computers, as well as various kinds of digital media players.

The processes and methods of the embodiments can be stored as instructions and/or data on non-transitory computer-readable media. The non-transitory computer readable medium may include any suitable computer readable medium, such as a memory, such as RAM, ROM, flash memory, or any other type of memory known in the art. In some embodiments, the non-transitory computer readable medium may include, for example, an electronic storage device, a magnetic storage device, an optical storage device, an electromagnetic storage device, a semiconductor storage device, or any suitable combination of such devices. More specific examples of the non-transitory computer readable medium may include a portable computer diskette, a floppy disk, a hard disk, magnetic disks or tapes, a read-only memory (ROM), a random access memory (RAM), a static random access memory (SRAM), a portable compact disc read-only memory (CD-ROM), an erasable programmable read-only memory (EPROM or Flash memory), electrically erasable programmable read-only memories (EEPROM), a digital versatile disk (DVD and DVD-ROM), a memory stick, other kinds of solid state drives, and any suitable combination of these exemplary media. A non-transitory computer readable medium, as used herein, is not to be construed as being transitory signals, such as radio waves or other freely propagating electromagnetic waves, electromagnetic waves propagating through a waveguide or other transmission media (e.g., light pulses passing through a fiber-optic cable), or electrical signals transmitted through a wire.

Instructions stored on the non-transitory computer readable medium for carrying out operations of the present invention may be instruction-set-architecture (ISA) instructions, assembler instructions, machine instructions, machine dependent instructions, microcode, firmware instructions, configuration data for integrated circuitry, state-setting data, or source code or object code written in any of one or more programming languages, including an object oriented programming language such as Smalltalk, C++, or suitable language, and procedural programming languages, such as the "C" programming language or similar programming languages.

Aspects of the present disclosure are described in association with figures illustrating flowcharts and/or block diagrams of methods, apparatus (systems), and computing products. It will be understood that each block of the flowcharts and/or block diagrams can be implemented by computer readable instructions. The flowcharts and block diagrams in the figures illustrate the architecture, functionality, and operation of possible implementations of various disclosed embodiments. Accordingly, each block in the flowchart or block diagrams may represent a module, segment, or portion of instructions. In some implementations, the functions set forth in the figures and claims may occur in an alternative order than listed and/or illustrated.

The embodiments may utilize any kind of network for communication between separate computing systems. A network can comprise any combination of local area networks (LANs) and/or wide area networks (WANs), using both wired and wireless communication systems. A network may use various known communications technologies and/or protocols. Communication technologies can include, but are not limited to: Ethernet, 802.11, worldwide interoperability for microwave access (WiMAX), mobile broadband (such as CDMA, and LTE), digital subscriber line (DSL), cable internet access, satellite broadband, wireless ISP, fiber optic internet, as well as other wired and wireless technologies. Networking protocols used on a network may include transmission control protocol/Internet protocol (TCP/IP), multiprotocol label switching (MPLS), User Datagram Protocol (UDP), hypertext transport protocol (HTTP), hypertext transport protocol secure (HTTPS) and file transfer protocol (FTP) as well as other protocols.

Data exchanged over a network may be represented using technologies and/or formats including hypertext markup language (HTML), extensible markup language (XML), Atom, JavaScript Object Notation (JSON), YAML, as well as other data exchange formats. In addition, information transferred over a network can be encrypted using conventional encryption technologies such as secure sockets layer (SSL), transport layer security (TLS), and Internet Protocol security (Ipsec).

Other systems, methods, features, and advantages of the disclosure will be, or will become, apparent to one of ordinary skill in the art upon examination of the following figures and detailed description. It is intended that all such additional systems, methods, features, and advantages be included within this description and this summary, be within the scope of the disclosure, and be protected by the following claims.

While various embodiments are described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature or element of any embodiment may be used in combination with or substituted for any other feature or element in any other embodiment unless specifically restricted.

This disclosure includes and contemplates combinations with features and elements known to the average artisan in the art. The embodiments, features, and elements that have been disclosed may also be combined with any conventional features or elements to form a distinct invention as defined by the claims. Any feature or element of any embodiment may also be combined with features or elements from other inventions to form another distinct invention as defined by the claims. Therefore, it will be understood that any of the features shown and/or discussed in the present disclosure may be implemented singularly or in any suitable combination. Accordingly, the embodiments are not to be restricted except in light of the attached claims and their equivalents. Also, various modifications and changes may be made within the scope of the attached claims.

We claim:

1. A method of identifying property damage in occluded aerial imagery, the method comprising:
receiving, at a damage classification system, first data including a first occluded image of a first property comprising at least a first structure, wherein the first structure is veiled in the first occluded image;
receiving, at the damage classification system, a training dataset, the training dataset comprising pairs of images, each pair including a first image and a second image, the first image providing a high visibility picture of a property, the second image providing a low visibility picture of the same property in the same position as in the first image;
wherein the second image is created employing an occlusion simulation engine that uses fractal expansion techniques to add occlusive features to the first image;
reducing a dynamic range of pixel intensities of the second image from a full intensity scale to a randomly compressed intensity scale;
feeding, at the damage classification system, the first occluded image to a generative model to generate a first reconstructed image in which the first structure is unveiled;
training, at the damage classification system, the generative model using the training dataset to produce high visibility pictures from occluded imagery;
extracting, at the damage classification system, a first feature from the first recon structed image;
estimating, by the damage classification system, damage to the first property based on at least the first feature;
classifying, by the damage classification system, the first property depicted in the first reconstructed image under a damage category based on the estimated damage; and
generating, at the damage classification system, a damage score for the first property based on the first reconstructed image; and
selecting, at the damage classification system, the damage category based on the damage score;
causing to be presented, at a computing device, the damage category, wherein at least a portion of the method is performed by a processing unit.

2. The method of claim 1, wherein the first occluded image is received from one of a drone, aircraft, and satellite further.

3. The method of claim 1, wherein the first structure is veiled in the first occluded image by one or more of the group comprising haze, smoke, rain, fog, and low lighting.

4. The method of claim 1, further comprising employing, at the damage classification system, a machine learning model to detect damage to the first structure in the first reconstructed image.

5. The method of claim 1, further comprising:
transmitting the first reconstructed image to one or a repair facility and an insurance representative.

6. The method of claim 5, wherein the damage score is greater than a pre-set damage threshold, and the method further comprises:
generating, at the damage classification system, an output indicating the damage score is above the threshold;
transmitting, from the damage classification system, the output to a claims processing module; and
causing, at the claims processing module and in response to the output, a payout signal to be generated that is configured to automatically release funds to a beneficiary of an insurance policy for the first property.

7. The method of claim 1, further comprising:
generating, at the damage classification system, an output describing the damage to the first property;
transmitting, from the damage classification system, the output to a claims processing module; and
causing, at the claims processing module and in response to the output, a preliminary claim to be generated that is configured to expedite a payout to a beneficiary of an insurance policy for the first property.

8. A method of clarifying occluded images to determine property damage, the method comprising:
receiving, at a damage classification system, a training dataset, the training dataset comprising pairs of images, each pair including a first image and a second image, the first image providing a high visibility picture of a property, the second image providing a low visibility picture of the same property in the same position as in the first image;
wherein the second image is created employing an occlusion simulation engine that uses fractal expansion techniques to add occlusive features to the first image;
reducing a dynamic range of pixel intensities of the second image from a full intensity scale to a randomly compressed intensity scale;
training, at the damage classification system, a generative model using the training dataset to produce high visibility pictures from occluded imagery;
receiving, at the damage classification system, first data including a first occluded image of a first property comprising at least a first structure, wherein the first structure is veiled in the first occluded image;
feeding, at the damage classification system, the first occluded image to the generative model to generate a first reconstructed image in which the first structure is unveiled;
generating, at the damage classification system, a damage score for the first property based on the first reconstructed image; and
selecting, at the damage classification system, the damage category based on the damage score; and
causing to be presented, at a computing device, the first recon structed image.

9. The method of claim 8, wherein the first data further includes a location of the first property, and the method further comprises causing to be presented, at the computing device, the first occluded image and information about an account associated with the location.

10. The method of claim 8, further comprising:
extracting, at the damage classification system, a first feature from the first recon structed image; and
estimating, by the damage classification system, damage to the first property based on at least the first feature.

11. The method of claim 10, further comprising classifying, by the damage classification system, the first property depicted in the first reconstructed image under a damage category based on the estimated damage.

12. The method of claim 11, further comprising causing to be presented, at the computing device, the damage category.

13. The method of claim 10, further comprising:
generating, at the damage classification system, an output describing the estimated damage to the first property;
transmitting, from the damage classification system, the output to a claims processing module; and
causing, at the claims processing module and in response to the output, a preliminary claim to be generated that is configured to expedite a payout to an owner of the first property.

14. A system for identifying property damage in occluded aerial imagery, the system comprising a processor and machine-readable media including instructions which, when executed by the processor, cause the processor to:
receive, at a damage classification system, first data including a first occluded image of a first property comprising at least a first structure, wherein the first structure is veiled in the first occluded image;
receive, at the damage classification system, a training dataset, the training dataset comprising pairs of images, each pair including a first image and a second image, the first image providing a high visibility picture of a property, the second image providing a low visibility picture of the same property in the same position as in the first image;
wherein the second image is created employing an occlusion simulation engine that uses fractal expansion techniques to add occlusive features to the first image;
reduce a dynamic range of pixel intensities of the second image from a full intensity scale to a randomly compressed intensity scale;
feed, at the damage classification system, the first occluded image to a generative model to generate a first reconstructed image in which the first structure is unveiled;
train, at the damage classification system, the generative model using the training dataset to produce high visibility pictures from occluded imagery;
extract, at the damage classification system, a first feature from the first recon structed image;
estimate, by the damage classification system, damage to the first property based on at least the first feature;
classify, by the damage classification system, the first property depicted in the first reconstructed image under a damage category based on the estimated damage;
generate, at the damage classification system, a damage score for the first property based on the first reconstructed image; and
select, at the damage classification system, the damage category based on the damage score; and
cause to be presented, at a computing device, the damage category.

15. The system of claim 14, wherein the instructions further cause the processor to:
transmit the first reconstructed image to one or a repair facility and an insurance representative.

16. The system of claim 14, wherein the first structure is veiled in the first occluded image by one or more of the group comprising haze, smoke, rain, fog, and low lighting.

17. The system of claim 14, wherein the instructions further cause the processor to employ, at the damage classification system, a machine learning model to detect damage to the first structure in the first reconstructed image.

18. The system of claim 14, wherein the first occluded image is received from one of a drone, aircraft, and satellite.

19. The system of claim 18, wherein the instructions further cause the processor to:
generate, at the damage classification system, an output indicating the damage score is above the threshold;
transmit, from the damage classification system, the output to a claims processing module; and
cause, at the claims processing module and in response to the output, a payout signal to be generated that is configured to automatically release funds to a beneficiary of an insurance policy for the first property.

20. The system of claim 14, wherein the instructions further cause the processor to:
generate, at the damage classification system, an output describing the damage to the first property;
transmit, from the damage classification system, the output to a claims processing module; and
cause, at the claims processing module and in response to the output, a preliminary claim to be generated that is configured to expedite a payout to a beneficiary of an insurance policy for the first property.

\* \* \* \* \*